United States Patent
Wang et al.

(10) Patent No.: US 10,821,174 B2
(45) Date of Patent: Nov. 3, 2020

(54) RECOMBINANT HANSENULA POLYMORPHA-BASED HIGH DOSAGE HEPATITIS B VACCINE

(71) Applicant: Hemu Wang, Tianjin (CN)

(72) Inventors: Hemu Wang, Tianjin (CN); Changhua Wang, Tianjin (CN); Jun Yang, Tianjin (CN)

(73) Assignee: Hemu Wang, Tianjin (CN)

( * ) Notice: Subject to any disclaimer, the term of this patent is extended or adjusted under 35 U.S.C. 154(b) by 32 days.

(21) Appl. No.: 16/088,255

(22) PCT Filed: Mar. 16, 2017

(86) PCT No.: PCT/CN2017/076929
§ 371 (c)(1),
(2) Date: Sep. 25, 2018

(87) PCT Pub. No.: WO2017/162090
PCT Pub. Date: Sep. 28, 2017

(65) Prior Publication Data
US 2019/0083608 A1   Mar. 21, 2019

(30) Foreign Application Priority Data
Mar. 25, 2016 (CN) .......................... 2016 1 0178526

(51) Int. Cl.
| *A61K 39/29* | (2006.01) |
|---|---|
| *C12N 9/88* | (2006.01) |
| *A61K 39/12* | (2006.01) |
| *A61P 31/20* | (2006.01) |
| *A61K 39/39* | (2006.01) |
| *C07K 14/02* | (2006.01) |
| *C12R 1/78* | (2006.01) |
| *A61K 39/00* | (2006.01) |

(52) U.S. Cl.
CPC ............ *A61K 39/292* (2013.01); *A61K 39/12* (2013.01); *A61K 39/29* (2013.01); *A61K 39/39* (2013.01); *A61P 31/20* (2018.01); *C07K 14/02* (2013.01); *C12N 9/88* (2013.01); *C12Y 401/01023* (2013.01); *A61K 2039/523* (2013.01); *A61K 2039/54* (2013.01); *A61K 2039/545* (2013.01); *A61K 2039/55505* (2013.01); *C12N 2730/10123* (2013.01); *C12N 2730/10134* (2013.01); *C12R 1/78* (2013.01)

(58) Field of Classification Search
None
See application file for complete search history.

(56) References Cited

U.S. PATENT DOCUMENTS 5,196,194 A * 3/1993 Rutter ............... C07K 14/005
424/189.1

FOREIGN PATENT DOCUMENTS

| CN | 1651570 A | 8/2005 |
|---|---|---|
| CN | 104232661 A | 12/2014 |

OTHER PUBLICATIONS

Janovicz et al. (Yeast. vol. 7, p. 431-443).*

* cited by examiner

*Primary Examiner* — Agnieszka Boesen
(74) *Attorney, Agent, or Firm* — Li & Cai Intellectual Property (USA) Office (57) ABSTRACT

Provided is a recombinant *Hansenula polymorpha*-based high dosage hepatitis B vaccine, an HBsAg pure stock solution yield of a recombinant *Hansenula polymorpha* fermentation broth used for producing the hepatitis B vaccine being 300 mg/L-400 mg/L.

11 Claims, 5 Drawing Sheets
Specification includes a Sequence Listing.

RECOMBINANT HANSENULA POLYMORPHA-BASED HIGH DOSAGE HEPATITIS B VACCINE

CROSS-REFERENCE TO RELATED PATENT APPLICATION

This application claims the benefit of priority to China Patent Application No. 201610178526.8, filed on Mar. 25, 2016 in People's Republic of China. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a field of genetic engineering, and more particularly to a hepatitis B vaccine product including hepatitis B surface antigens (HBsAg) expressed by recombinant *Hansenula polymorpha*, and the dosage of the hepatitis B vaccine product for adults is 40 μg/lmL, and for children is 20 μg/0.5 mL.

BACKGROUND OF THE DISCLOSURE

HBV (hepatitis B virus, HBV) infection is a serious public health problem. According to the World Health Organization (WHO), about 20 million people have been infected with HBV within 6 billion people worldwide, of which 350 million people have chronic HBV infection; about 1 million people die each year from liver failure, cirrhosis and primary hepatocellular carcinoma (liver cancer) caused by HBV infection. Liver cancer patients worldwide, more than 75% is caused by HBV. China is an endemic area of HBV infection. The Ministry of Health of China incorporated hepatitis B vaccine into planned immunization management in 1992. In December 2001, the State Council of China officially approved the immunization of hepatitis B vaccine into children's programs, requiring all neonates in all provinces and autonomous regions vaccinated hepatitis B vaccine for free (except for a small fee) since 2002. According to the plan immunization regulations formulated in March 2005, from Jun. 1, 2005, offered free hepatitis B vaccine to all neonates. After nearly 15 years of efforts, the general population in China, especially children under the age of 15, HBV infection rate has significantly decreased. According to the national hepatitis B serological surveys in 2006, the carrying rate of hepatitis B surface antigen (HBsAg) in the whole population has decreased from 9.75% to 7.18% since 1992, and the hepatitis B surface antigen carrying rate in children under 5 years old has been decreased from 9.67% to 0.96%. Based on projections, about 93 million people are suffering from chronic HBV infection in China, including about 20 million patients with chronic hepatitis B. It is estimated that liver cirrhosis and liver cancer due to HBV cause nearly 300,000 death cases each year, wherein new hepatitis B are about 0.5 to 1 million cases. Therefore, HBV disease is an important factor that endangers people's health, hinders social development, and affects social stability for a long time. It is a serious public health problem in people-oriented society, and also a priority major health issue in China. The prevalence of HBV infection in Chinese population is high, which brings a heavy economic burden to the country. According to the survey, the annual direct and indirect medical expense for chronic hepatitis B (including liver cirrhosis and liver cancer) in China is about 680 billion. Hepatitis B vaccine immunization prevention is the most effective way to reduce the burden of disease.

Gene recombination technology is the core technology of modern biotechnology; also is the mainly technology of the large-scale production of hepatitis B vaccine, and the only technology of virus-like particle hepatitis B virus surface antigen (HBsAg VLP). In the 1970s, the first microbial genetic recombination technology developed was the *E. coli* expression system in prokaryotic cells. However, due to its lack of post-translational processing and modification in eukaryotic cells; it only expresses HBsAg linear antigen, which is too weak to cause immunization, and cannot be assembled into HBsAg VLP antigens, so that it has failed after nearly 10 years research. In the 1980s, yeast as a single cell eukaryotic microorganism, which has many advantages such as being easy to large scale fermentation and simple genetic manipulation as the characteristics of prokaryotic organisms, and has the characteristics of post-translational processing and modification functions of mammalian cells for producing biological active protein of eukaryotic cells. *Saccharomyces cerevisiae* was the first eukaryotic system to express foreign genes. Merck first successfully expressed HBsAg VLP antigen; the first recombinant hepatitis B vaccine and the first anti-cancer vaccine were successfully developed. However, there are still many shortcomings in the industrial production of *S. cerevisiae* expression system. For example, the exogenous gene plasmids of engineering strain are free in the cytoplasm lead to genetically unstable; the fermentation density is not enough to low production efficiency; the synthesized polypeptide chain is often hyper-glycosylated. In 1986, Merck's *S. cerevisiae* recombinant HBsAg pure stock solution yield was 10 mg/L; the dosage of the recombinant hepatitis B vaccine was determined to be 5 μg/dose limited by the HBsAg particle antigen production at that time. In 1995, Beijing Tiantan and Shenzhen Kangtai imported from the US Merck introduced the *S. cerevisiae* recombinant hepatitis B vaccine into the 800 liters production of fermentation scale. According to Merck's standard, 3 g of pure HBsAg virus-like particle antigen can be produced per liter of fermentation broth; the annual yield is 5 μg/dose for 20 million needles. After nearly a decade of process improvement, the pure stock solution of HBsAg virus-like particle antigen per liter of fermentation broth has been increased to 10 mg. In 1989, the *S. cerevisiae* recombinant hepatitis B vaccine developed by Shike Company, the yield of HBsAg VLP pure stock solution was multiplied to 20 mg/L, so the dosage of adult was 20 μg/dose and the child dosage was 10 μg/dose. In the early 1990s, Chinese scientists successfully developed a hepatitis B vaccine from recombinant CHO cells, which has the advantage that recombinant HBsAg VLP granule antigens can be directly secreted into the extracellular. However, the animal cells need to be shaken and cultured, and the yield is low. Only 1 mg of the HBsAg VLP pure stock solution can be collected per liter of culture. In 1995, the *Hansenula polymorpha* recombinant hepatitis B vaccine was developed by Germany TUV Rheinland, the yield of HBsAg VLP pure stock solution was raised to 60 mg/L; the yield increased several times. In 2004, it was put into production in Korea, and the adult dosage was still 20 µg/dose, the child dosage was also 10 µg/dose. This patentee has been engaged in research and development of *Hansenula polymorpha* recombinant hepatitis B vaccine since 1995. In 1998 to 2002, in Dalian Gaoxin Bio-Pharmaceutical Co., Ltd., the Hans Yeast recombinant HBsAg adw hepatitis B vaccine was developed. The yield of HBsAg VLP pure stock solution was 40 mg/L, and it has been approved since 2002 in china. In 2003 to 2006, the applicant assisted Beijing Tiantan Biological Products Co., Ltd. to develop recombinant *Hansenula polymorpha* HBsAg-adr2 hepatitis B vaccine. The pure stock solution of HBsAg VLP has a yield of 85 mg/liter or more; it has been submitted to the National New Drug Review in 2015, and the China patent publication number based on the vaccine is CN104232661A. In view of the fact that the existing hepatitis B vaccine is limited to the production of hepatitis B surface antigen (HBsAg) and the need for universal vaccination of hepatitis B vaccine, the existing hepatitis B vaccine generally adopts the above-mentioned low dosage vaccination program.

Currently, the pilot case of the immune response of hepatitis B vaccine in China is based on the following two sets of clinical studies. The immune response of anti-HBs are detected by gold chemiluminescence microparticle immunoassay with large sample size and strict management as following standard analysis results: (1) In Shanghai, 1531 newborns were inoculated with 5 µg/dose *S. cerevisiae* recombinant hepatitis B vaccine in 0, 1 and 6 months in 2011; the low/non response rate of Anti-HBs immune response was up to 21.68%. Geometric mean titer (GMT) is only 282.34 mIU/ml. At the same time, 516 newborns were inoculated with 10 µg/dose *Hansenula polymorpha* recombinant hepatitis B vaccine at 0, 1, and 6 months; the low/non response rate was 3.10%, and the GMT was 1408.08 mIU/ml. (2) In Shandong, two recombinant hepatitis B vaccines were respectively inoculated in adult susceptible populations in 0, 1, and 6 months in 2013. 2,011 people were inoculated with GSK *Saccharomyces cerevisiae* recombinant hepatitis B vaccine with 20 µg/dose. The anti-HBs low/no response rate was up to 29.79%, and GMT was only 270.39 mIU/ml. Another 2,290 people were inoculated with Huabei Pharmaceutical Jintan CHO recombinant hepatitis B vaccine 20 µg/dose. The anti-HBs low/non-response rate was also as high as 28.43%, and GMT was only 312.67 mIU/ml.

Above results show that among the four major hepatitis B vaccines in China, only the newborn *Hansenula polymorpha* recombinant hepatitis B vaccine is ideal. The low/non response average rate of other three major varieties: 5 µg/dose newborn *Saccharomyces cerevisiae* recombinant hepatitis B vaccine, 20 µg/dose adult *S. cerevisiae* recombinant hepatitis B vaccine and 20 µg/dose adult CHO recombinant hepatitis B vaccine are all up to 30%, and GMT are all as low as 300 mIU/ml. In particular, there are currently no hepatitis B vaccine varieties suitable for adults in China. As Dr. Dong Shengfu of Fudan University and Dr. Li Pingli of Shandong University believe that the hepatitis B vaccine currently still has weak immunogenicity. Market demand drives the development of high-immunity hepatitis B vaccine, and determines developing direction of the following high-dose products of hepatitis B vaccine: the dosage of hepatitis B vaccine for children is 20 µg/dose, and the three needles are inoculated by 0, 1, and 6 months respectively. The GMT of the anti-HBs immune response is expected ≥2000 mIU/ml, the low/non response rate (<100 mIU/ml)<5%, and the high response rate (≥1000 mIU/ml) >60%. The dosage of hepatitis B vaccine for adult is 40 µg/dose, and the three needles are inoculated by 0, 1, and 6 months respectively. The anticipation GMT of anti-HBs immune response is expected: GMC>1000 mIU/ml, low/non response rate (<100 mIU/ml)<5%, high response rate (≥1000 mIU/ml)>50%.

Based on the results of the epidemiological survey of hepatitis B virus in the national population in 1992 and 2006, we conduct a more in-depth interpretation of the changes in the HBsAg carrying rate among people aged 5 years older to further predict the total demand for hepatitis B vaccine in China, so as to determine the total demand for the above-mentioned high-dose hepatitis B vaccine, we have to control the problems of hepatitis B vaccine among the overall national population. (1) Due to the planned immunization of hepatitis B vaccine for all newborns in China is free, the hepatitis B surface antigen carrying rate of children under 5 years old has dropped from 9.67% to 0.96%; the number of HBsAg carriers in China has decreased by 22 million for a great contribution. However, the current newborn vaccination against hepatitis B vaccine is immunized from 2006 to the next 15 years, 2021, the rate of hepatitis B surface antigen carrying in children under 5 years old is already low, the contribution of HBsAg carrying rate has ceased to exist. (2) In 2006, children under the age of 5 years old, under 10 years old, and under 15 years old, the hepatitis B virus surface antigen (HBsAg) carrying rate increased rapidly from 0.96% to 1.96% and 3.37% respectively, especially the coverage of surface antigen (HBsAg) carrying rates in children of these ages was increasing even more in the 12 provinces (Anhui, Fujian, Jiangxi, Guangdong, Guangxi, Hainan, Chongqing, In Tibet, Jiangsu, Zhejiang, Hubei, and Sichuan) in China where hepatitis B virus was highly endemic (surface antigen (HBsAg) carrying rate >8.0%). The reason may be that the low/non-response rate of anti-HBs in children with hepatitis B vaccine was high. It was recommended that neonatal immunization in high-endemic areas should be 20 µg/dose for three needles it can further improve the anti-HBs protection response and reduce the low/non-response rate. The vaccine demand was about 6 million (3 needles) per year. (3) The HBsAg carrying rate of people under the age of 15 to 20 years old is rapidly from 3.37% to 7.21%. Reports have shown that after the priming response of children with hepatitis B vaccine, the effective protection period lasts for 10 to 14 years due to immune memory. For the above-mentioned children aged 10 to 14 years old who have passed the immune memory protection period, in order to increase the immune protection, the *Hansenula polymorpha* recombinant hepatitis B vaccine should be re-inoculated at 20 µg/dose for three needles in the procedures of 0, 1, and 6 months. To ensure that the HBsAg carrying rate of people under 10 to 20 years old in China is controlled below 3.00%; the continuous implementation of 15 years can contribute to the reduction of the number of HBsAg carriers in our population by 9 million. The demand for vaccines is about 18 million per year (three needles). (4) The HBsAg carrying rate of the population aged 15 to 59 years old is still as high as 8.57%. The hepatitis B vaccination rate of the population is only 13.78%. Firstly, the high-risk adult population and susceptible population should be inoculated with 40 µg/dose *Hansenula polymorpha* recombinant HBsAg hepatitis B vaccine for three needles without screening. The final coverage of adult hepatitis B vaccine is achieved. The aged 15 to 59 years old in China are total 1 billion people, and then it takes 7 to 8 years to complete the full coverage of hepatitis B vaccine vaccination for 120 to 150 million people per year. Then, according to the immune memory cycle of 10 years, 40 µg/dose Hansenula polymorpha recombinant HBsAg hepatitis B vaccine for three needles are re-inoculated according to the procedures of 0, 1, and 6 months respectively at 20, 30, 40 and 50 years old. For 10 consecutive years, it is expected that the HBsAg carrying rate of people aged 15 to 59 years old will be controlled at around 6.00%; this will contribute to the reduction of the number of HBsAg carriers in China by 20 million. In summary, it is great significance to improve the prevention effect of hepatitis B in China by providing a highly immunogenic, high-dose recombinant hepatitis B vaccine.

SUMMARY OF THE DISCLOSURE

In response to the above-referenced technical inadequacies, the present disclosure provides a high dosage of hepatitis B vaccine based on recombinant *Hansenula polymorpha*. The hepatitis B surface antigen (HBsAg) pure stock solution yield used for producing the hepatitis B vaccine is 300 mg/L to 400 mg/L, and the dosage of hepatitis B surface antigen (HBsAg) of the hepatitis B vaccine is 40 μg/dose or 20 μg/dose, 40 μg/dose dosage is for adults, and 20 μg/dose dosage is for children.

In certain embodiments, the DNA sequence of the HBsAg expressed by the recombinant *Hansenula polymorpha* is shown in SEQ ID NO: 1. The hepatitis B surface antigen is adw subtype.

In certain embodiments, the amino acid sequence of the HBsAg expressed by the recombinant *Hansenula polymorpha* is shown in SEQ ID NO: 2.

In certain embodiments, the HBsAg expressed by the recombinant *Hansenula polymorpha* is a virus-like particle structure, which is formed by inserting HBsAgs into *Hansenula polymorpha* lipid. In addition, 9 to 12 among the 14 cysteic acids of the HBsAg form disulfide bonds.

In certain embodiments, the host *Hansenula polymorpha* cell line of the recombinant *Hansenula polymorpha* is HU-11 (CGMCC No. 1218), and the disrupted DNA sequence of the orphanin-5-phosphate decarboxylase gene of the host *Hansenula polymorpha* is shown in SEQ ID NO: 3.

In certain embodiments, the hepatitis B vaccine further includes an adjuvant; the adjuvant is aluminum adjuvant prepared by in-situ coprecipitation or the direct adsorption. Preferably, the aluminum adjuvant is prepared by in-situ coprecipitation.

In certain embodiments, the immunization procedure of the hepatitis B vaccine is one injection respectively in 0, 1, 2 to 12 months for three needles. Preferably, the immunization procedure is one injection respectively in 0, 1, and 6 months for three needles.

In certain embodiments, the dosage form of the hepatitis B vaccine comprises a prefilled injection solution, an injection solution or a lyophilized powder injection; the dosage form is preferably the prefilled injection solution.

In one aspect, the present disclosure provides a recombinant *Hansenula polymorpha*, which includes the nucleotide sequence of SEQ ID NO: 1, and the nucleotide sequence of SEQ ID NO: 1 is integrated into the genome of the recombinant *Hansenula polymorpha*.

In certain embodiments, the host *Hansenula polymorpha* cell line of the recombinant *Hansenula polymorpha* is HU-11 (CGMCC No. 1218), and the disrupted DNA sequence of the orphanin-5-phosphate decarboxylase gene of the host *Hansenula polymorpha* is shown in SEQ ID NO: 3.

Figure 4:
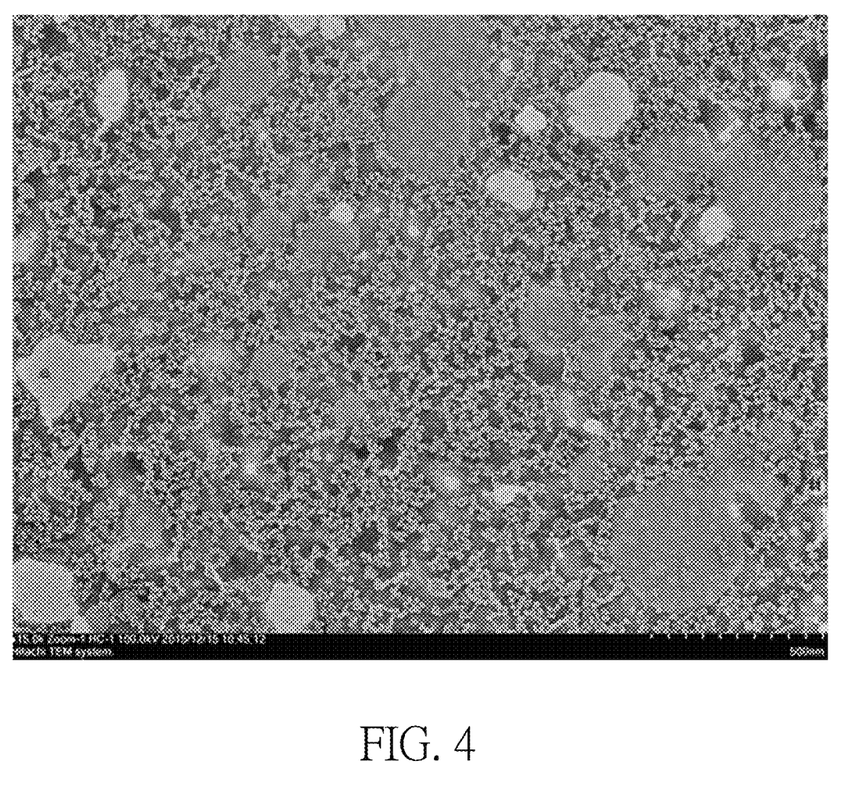
FIG. 4 is an electron micrograph of the pure stock solution of recombinant *Hansenula polymorpha* recombinant HBsAg.

The present disclosure provides a high dosage hepatitis B vaccine based on recombinant *Hansenula polymorpha*, and provides a high-yield recombinant *Hansenula polymorpha* strain with high VLP antigen by screening, and improve the yield and quality of hepatitis B surface antigen. The dosage of the high dosage hepatitis B vaccine provided in the present invention for adult is 40 μg/dose and for children is 20 μg/dose. When the production scale (two 800 liter fermenters) of *Hansenula polymorpha* recombinant HBsAg VLP pure stock solution access to 19,800 grams, the production capacity of the hepatitis B vaccine can produce 330 million needles (110 million people) for adult with 40 μg/dose and 330 million needles (110 million people) for children with 20 μg/dose to 330 million needles (110 million people). This production can meet the demand for full coverage immunization in all populations in China. Meanwhile, the present disclosure provides an improved nucleotide sequence (SEQ ID NO: 1) and encoding polypeptide thereof (SEQ ID NO: 2) based on the conventional HBsAg nucleotide sequence. Compared with the conventional HBsAg nucleotide sequence, the improved sequence can generate high-purity HBsAg VLP and high-yield recombinant *Hansenula polymorpha* engineering strains by easy selection. Electron microscopy (FIG. 4) shows that HBsAg produced by recombinant *Hansenula polymorpha* engineering strains with improved sequences is a high-quality VLP that induce good immune response. Moreover, the purity of HBsAg production is high up to 97.2% under the pilot condition, and under the large-scale production conditions, the purity standard of 99% can be achieved. Further, the present disclosure provides a hepatitis B vaccine priority product prepared as prefilled injection liquid, and the prefilled syringe has one needle in one box, which is convenient and easy to use for a disposable syringe. Vaccination does not require a separate syringe to prevent the glass syringes infections, spreading infectious diseases or improper needle selection, and avoiding the risk of repeat use. The experiment proved that the routine repacking of recombinant hepatitis B vaccine with prefilled injection under the heat stability test at 37° C. for 45 days can met the in vitro relative efficacy (RP) requirements, while the conventional split hepatitis B vaccine under the same storage conditions cannot met RP requirement.

The recombinant hepatitis B vaccine packed in the prefilled syringe can be stored, used, and transported out of the cold chain in a short time. It is expected to increase the timely vaccination rate of hepatitis B vaccine within 4.8 million newborns born in old, small, border and poor areas every year. The full-time vaccination of hepatitis B vaccine with prefilled syringes has a good overall cost-benefit ratio.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the detailed description and the accompanying drawings, in which.

DETAILED DESCRIPTION OF THE EXEMPLARY EMBODIMENTS

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

The Construction of the *Hansenula polymorpha* Intracellular Plasmid pMPT-02 is the Applicant's Non-Exclusive Proprietary Technology:

1.5 kb *Hansenula polymorpha* MOX (methanol oxidase) promoter, 350 bp *Hansenula polymorpha* MOX (methanol oxidase) terminator, 1.0 kb *Hansenula polymorpha* autonomous replication sequence HARS, and 1.1 kb *Saccharomyces cerevisiae* uracil gene ScURA3 were tightly ligated by gene synthesis technology element, and then inserted into the pBluescripII plasmid to construct a shuttle plasmid pMPT-02.

Development of the Host Cell Using the Uracil Auxotrophic URA3-Host Cell Line HU-11:

A recombinant *H. polymorpha* strain HU-11 (The accession number for the deposit: CGMCC No. 1218. The date of the deposit: Sep. 13, 2004. The name and address of the depository: China General Microbiological Culture Collection Center (CGMCC), No. 1 West Beichen Road, Chaoyang District, Beijing 100101, China) in which the orotidine-5-phosphate decarboxylase gene (HURA3) was disrupted by homologous sequence-mediated homologous integration. Compared with the conventional auxotrophic host strains produced by mutagenesis, the recombinant *H. polymorpha* strain HU-11 has the characteristics of high genetic stability and low back mutation rate. It was convenient for genetic transformation and screening of recombinant strains, and maintains the wild-type strain. The physiological and biochemical characteristics were beneficial to the culture of recombinant strains and the high expression of foreign proteins, and have high industrial application value. The DNA sequencing result of the disrupted URA3 gene of the Hansenula polymorpha host strain HU11 showed that the five bases of GAAGT were inserted into the 31st base. The insertion of five bases of GAAGT produces a frameshift mutation. The frameshift mutation resulted in a mutation in all of the 254 amino acid codes after the 11th position, and the mutation produced a total of 15 termination codes, indicating that the structural gene of URA3 is no longer re-expressible. The probability that the five bases GAAGT simultaneously produce a back reversion mutation was extremely small. The experimental test also proved that the back mutation rate of the host strain HU11 is zero. This low back-reversion mutation rate of the host strain was particularly advantageous for transformation screening. URA3-ogal deficiency host cell line HU-11 (CGMCC No. 1218) established by gene knock out technology was disclosed in the applicant's previously invention CN1651570A. The DNA sequence in which the disrupted decarboxylase gene (HURA3) was shown in SEQ ID NO:3.

The DNA sequence of HBsAg expression of the recombinant *Hansenula polymorpha* of the present disclosure was based on the HBsAg adw2 subtypes as shown in SEQ ID NO: 1. The amino acid sequence of the HBsAg is shown in SEQ ID NO: 2.

Construction of the *Hansenula polymorpha* Intracellular Plasmids pMPT-HBs adw2 (See FIG. 1):

A synthetic nucleotide sequence according to the sequence shown in SEQ ID NO: 1 (hereinafter referred to as HBsAg adw2 gene) was constructed into a glycerol strain containing the HBsAg adw2 gene plasmid; the plasmid after correct sequencing was digested with EcoRI/BamHI, and then 701 bp DNA fragment was obtained.

The correct plasmid pMPT-02 was digested with EcoRI/BamHI, and the vector DNA obtained after the gelatinization was ligated to obtain the *Hansenula polymorpha* intracellular plasmid pMPT-HBs adw2, and the plasmid pMPT-HBs adw2 was heat shock transformed into *E. coli* Competent Cell JM109 (Code No. D9052), and then was cultured overnight by plating. Single colonies were selected from the transformation plates, plasmid DNA was extracted and digested with EcoRI/BamHI, and the results of restriction enzyme digestion showed positive clones. Sequencing confirmed that the plasmid pMPT-HBs adw2 was correct.

Figure 1:
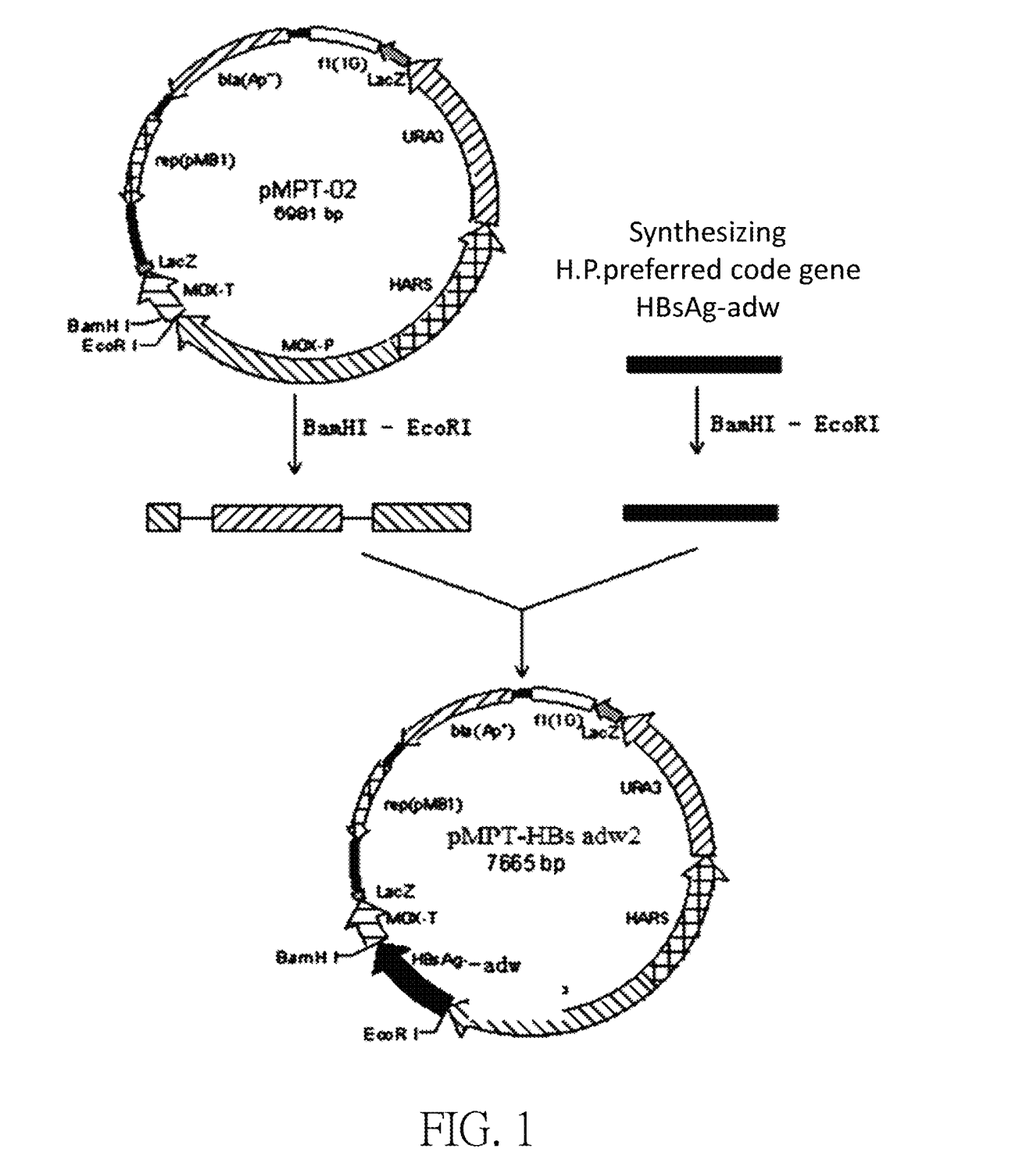
FIG. 1 is a schematic view showing the construction process of plasmid pMPT-HBs adw2.
Figure 2:
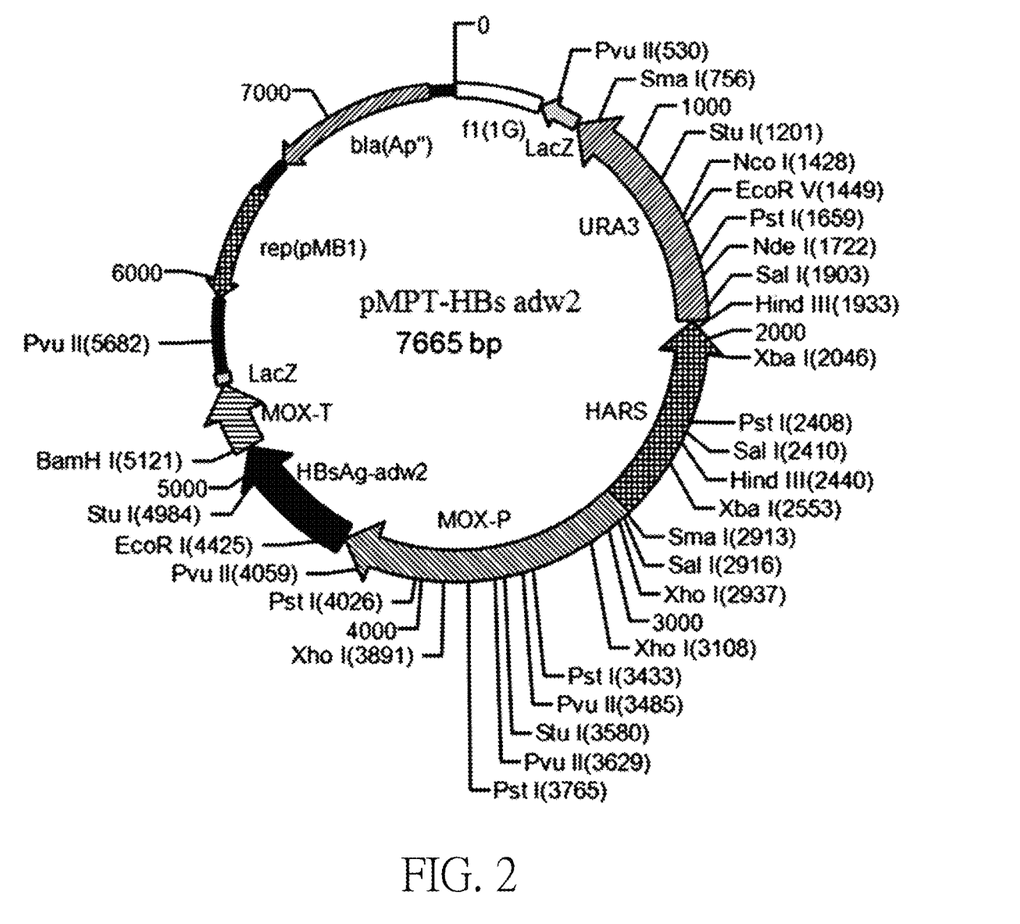
FIG. 2 is a physical map of plasmid pMPT-HBs adw2.

The HBsAg adw2 gene was inserted into the multiple cloning site of the *Hansenula polymorpha* expression system intracellular plasmid pMPT-02: between EcoRI and BamHI. The full length of the plasmid pMPT-HBs adw2 is 7665 bp. A schematic diagram of the construction process of plasmid pMPT-HBs-adw2 is shown in FIG. 1. The physical map of the pMPT-HBs adw2 plasmid is shown in FIG. 2.

Construction of Recombinant *Hansenula polymorpha* Hepatitis B Virus Surface Antigen (HBsAg) Adw2 Subtype Engineering Strain:

In order to construct the recombinant *Hansenula polymorpha* hepatitis B virus surface antigen (HBsAg) adw2 subtype engineering strain, the cell electroporation technology developed by the applicant was applied. The RC pulse: amplitude 1500V, capacitance 22 μF, and time constant 3-5 ms electric shock 1 time, adopted the pMPT-HBsadw2 plasmid transformed into *Hansenula polymorpha* cells of the HU-11 strain (CGMCC No. 1218) from which the URA3-gene was knocked out. The single colony transformants were picked up on the MD selection culture plate and transferred to the MD liquid medium for continuous subculture. The adw2 subtype HBsAg gene and the corresponding regulatory components were multi-copy and heterologously integrated into the host *Hansenula polymorpha* cell chromosome. After a single colony of more than one thousand transformant single colonies, the following three steps were screened:

(1) Clonal strains with large single colonies and fast cell growth have a high probability of multiple copies.

(2) The PCR technique was used to compare the electrophoretic band luminance of the HBsAg gene and the single copy number MOX (methanol oxidase) gene, and the HBsAg gene copy number was determined semi-quantitatively.

(3) The expression level of HBsAg released after methanol-induced and shake flask culture for 72 hours was detected.

The application of PCR technology to transformants screening was a new creation of this application. The multiple copies of the foreign gene HBsAg are determined and heterologously integrated in the *Hansenula polymorpha* chromosome, while the MOX gene in the *Hansenula polymorpha* chromosome was intact and not destroyed. They all play an important role and show unique advantages of the *Hansenula polymorpha* expression system. A pair of primers were designed to simultaneously amplify the MOX gene (single copy) and the heterologous integrated HBsAg foreign gene (multicopy) in the *Hansenula polymorpha* chromosome. By comparing the brightness of the bands of the amplified product in agarose gel electrophoresis, it was possible to roughly determine whether the HBsAg gene was multiple copies. This method was used for the preliminary screening of multi-copy strains of engineered HBsAg gene. The amplified HBsAg fragment was 800 bp in length and the amplified MOX fragment was 2000 bp in length.

Design Using Primer Sequences:

```
primer forward:   5'-TCAAAAGCGGTATGTCCTTCCACGT-'3
primer reverse:   5'-TACTGCTGCCAGTGCACGGTG-'3
```

Figure 3:
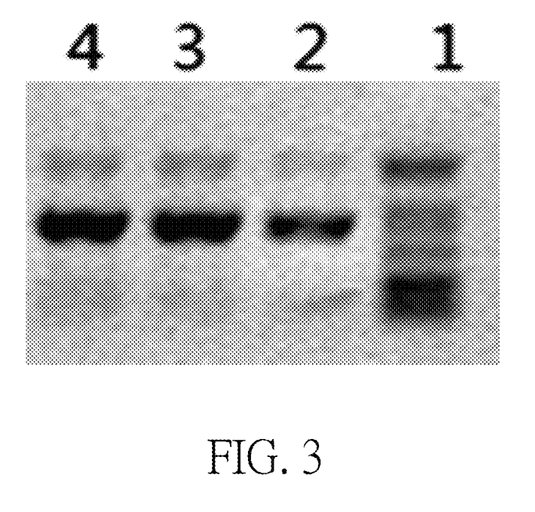
FIG. 3 is an electrophoresis photograph of a PCR amplification product of the engineered strain obtained by screening from over 100 copies transformant.

PCR product agarose gel electrophoresis: the amplified product of HBsAg gene of engineering bacteria was about 800 bp, and the amplification product of Hansen yeast single copy gene MOX gene was about 2000 bp. The electrophoresis photograph of the PCR amplification product of the engineered strain obtained by screening from over 100 copies transformant was shown in FIG. 3, wherein 1 was Marker.

The obtained engineering strain was tested by using 30 liters of pilot fermentation to express the HBsAg content expressed by recombinant *Hansenula polymorpha* in three batches of fermentation stock solution:

The protein concentration was measured by the Lowry method protein quantitative kit according to national standards. The standard product was bovine serum albumin provided by the kit, and the regression curve: $y=1.0368x-0.0109$ and $R2=0.999$. The fermentation stock solution was diluted 5 times with physiological saline, and the absorbance was measured. Each batch was tested twice, and the concentration of HBsAg in the corresponding pure stock solution was calculated, and the yield of HBsA was calculated as shown in the following table.

| batch number | 750 nm Absorbance value | HBsAg concentration | HBsAg average concentration (mg/mL) | Fermentation liquid volume (mL) | HBsAg yield (mg/L) Fermentation liquid |
|---|---|---|---|---|---|
| Pure 20150606 | 0.306 0.312 | 1.491 1.563 | 1.527 | 260 | 397 |
| Pure 20150617 | 0.253 0.258 | 1.257 1.283 | 1.270 | 260 | 330 |
| Pure 20150624 | 0.276 0.281 | 1.376 1.402 | 1.395 | 260 | 363 |

The purity of the recombinant *Hansenula polymorpha* HBsAg was analyzed by high pressure liquid chromatography, and the purity of the recombinant HBsAg pure stock solution was over 97%. An electron micrograph of the pure stock solution of recombinant *Hansenula polymorpha* recombinant HBsAg was shown in FIG. 4. The results showed that the high purity, high concentration and virus-like particle (VLP) structure of recombinant HBsAg were stable.

New Product of Hepatitis B Vaccine with Recombinant *Hansenula Polymorpha* HBsAg for Adult was 40 μg/Dose and for Children was 20 μg/Dose:

In 2010, the European Hepatitis B Immunology Consensus Group reported that hepatitis B surface antigen (HBsAg) immunization was the basis for anti-hepatitis B immunity. Anti-HBs were detected after inoculation to assess the intensity of the immune response in history. Although 10 mIU/ml was usually taken as a protective response, low levels of anti-HBs mask significant HBsAg infection. This led to some countries (eg, the United Kingdom, 1996) using a higher protective response of 100 mIU/ml; anti-HBs<100 mIU/ml was judged to be low/non response.

On this basis, after the prophylactic hepatitis B vaccine immunization formed in recent years, the international grading standard for serological detection of protective anti-HBs response level: anti-HBs<10 mIU/ml is judged as non-response; 10 mIU/ml≤anti-HBs<100 mIU/ml was judged as low response; 100 mIU/ml≤anti-HBs<1000 mIU/ml was judged as a normal response; and anti-HBs≥1000 mIU/ml was judged as a high response.

As mentioned above, according to the above four major hepatitis B vaccines in China, only the anti-HBs response level of the 10 μg/dose newborn *Hansenula polymorpha* recombinant hepatitis B vaccine fully complies with the above classification criteria. The other three varieties: 5 μg/dose newborn *S. cerevisiae* recombinant hepatitis B vaccine, 20 μg/dose adult *S. cerevisiae* recombinant hepatitis B vaccine and 20 μg/dose adult CHO recombinant hepatitis B vaccine, all had a low/non response rate of up to 30%, and the average titer GMT was low at 300 mIU/ml. In particular, there were currently no hepatitis B vaccine varieties suitable for adults in China. The market demand for recombinant hepatitis B vaccine, which was urgently needed to develop high anti-HBs immune response; it has become the driving force for *Hansenula polymorpha* recombinant HBsAg in adult for 40 μg/dose and in children for 20 μg/dose.

The practice showed that the anti-HBs response level of hepatitis B vaccine is dose-dependent of HBsAg antigen, which is a common "ubiquitous curve relationship." As the dose of HBsAg antigen increases gradually, the response level of Anti-HBs increases slowly. After the dose of HBsAg antigen increased to a certain point, the anti-HBs response level entered a rapidly growing linear region; in the linear region, antigen doubling induced an increase in the anti-HBs response several times; in the linear region, the HBsAg antigen dose had at least four doubling points. When the dose of HBsAg antigen increased again, the level of Anti-HBs response turned to a slow increase. Therefore, the dose of HBsAg antigen for children and adult vaccines should be selected in the corresponding linear phase of the rapid response of the response curve. If the children's HBsAg antigen dosage was 5 μg/dose at the 2nd doubling point of the linear region, the HBsAg antigen dose was 10 μg/dose at the 3rd doubling point; when the children's HBsAg antigen dosage was doubled to 20 μg/dose at the 4th doubling point, the Anti-HBs response level still had several times the potential to increase. The above-mentioned hepatitis B vaccine anti-HBs response level and the dose of the HBsAg was dose-dependent relationship, which became a new hepatitis B vaccine product for determining the anti-HBs response rate of Hansenula polymorpha recombinant HBsAg adult dose of 40 μg/dose and children dose of 20 μg/dose for an important theoretical basis. The anti-HBs response of the above Hansenula polymorpha recombinant HBsAg hepatitis B vaccine product was expected to: geometric mean titer for all adults aged 15-59: GMC>Anti-HBs1000 mIU/ml, low/non response rate (<Anti-HBs 100 mIU/ml)<5%, high response rate (≥Anti-HBs 1000 mIU/ml)>50%; geometric mean titers of neonates with high prevalence of HBsAg and older children aged 10-13: GMC>Anti-HBs 2000 mIU/ml, low/non response rate <5%, and high response rate >60%.

The yield of HBsAg pure stock solution of the recombinant Hansenula polymorpha provided by the present invention reached 300 mg/liter or more, and the yield of the purified HBsAg pure stock solution of the existing Hansenula polymorpha or brewer's yeast was much higher than 5 times to 30 times; the highest level in the world today, a new breakthrough in genetic recombination technology. The annual production of recombinant HBsAg pure stock solution was calculated on the scale of two fermenters with 800 liter:

2 products (raw liquid liter (working volume)× (working volume) liter (work tank/year)=19,800 g/year It was a prerequisite for the large-scale production of hepatitis B vaccine with Hansenula polymorpha recombinant HBsAg adult dose of 40 μg/dose and children dose of 20 μg/dose. When the annual yield of Hansenula polymorpha recombinant HBsAg VLP pure stock solution reaches 19,800 grams, the dosage of Hansenula polymorpha recombinant HBsAg for adult was 40 μg/dose and the annual output of hepatitis B vaccine was 330 million needles (110 million people); the dosage of Hansenula polymorpha recombinant HBsAg for children was 20 μg/dose and the annual output of hepatitis B vaccine was 330 million needles (110 million people); it will become the largest manufacturer of recombinant hepatitis B vaccine in the world for meet the demand of expansion of immunization for all populations in the country.

First Embodiment

The pMPT-HBsAg adw2 plasmid was constructed based on the sequence of SEQ ID NO: 1. The construction of plasmid pMPT-HBs adw2 includes the following steps:

The HBsAg adw2 gene was synthesized according to the DNA sequence of Hansenula polymorpha preferred code HBsAg adw2; and the glycerol strain containing the HBsAg adw2 gene plasmid was constructed and named as MC407B-16.

The correctly sequenced MC407B-16 plasmid was digested with EcoRI/BamHI, and the digested product was used a TaKaRa PCR Fragment Recovery Kit (Code No. D301) to recover 701 bp DNA fragment called Inset DNA6.

The correct plasmid pMPT-02 was digested with EcoRI/BamHI, and the vector DNA obtained after the gel was recovered was called Vector DNA6.

Inset DNA6 was ligated to Vector DNA6 using Solution in TaKaRa DNA Ligation Kit (Code No. D6022), and then heat-shock transformed into E. coli Competent Cell JM109 (Code No. D9052), and the cells were cultured overnight.

Single colonies were selected from the transformation plates, and plasmid DNA was extracted and digested with EcoRI/BamHI. The results showed that MC407A+B+C+D-7780 were positive clones.

The plasmid MC407A+B+C+D-77 was sequenced respectively with primers RV-M, M13-47, MC407P1, MC407P2, MC407P3, MC407P4, MC407P5, MC407P6, MC407P7, MC407P8, MC407P9, MC407BF11, MC407BR11 to prove the plasmid pMPT-HBs adw2 were correct.

Second Embodiment

Construction of a Hansenula polymorpha recombinant HBsAg engineering strain (i.e., a Hansenula polymorpha host cell transformation screening strain comprising the sequence set forth in SEQ ID NO: 1).

Figure 5:
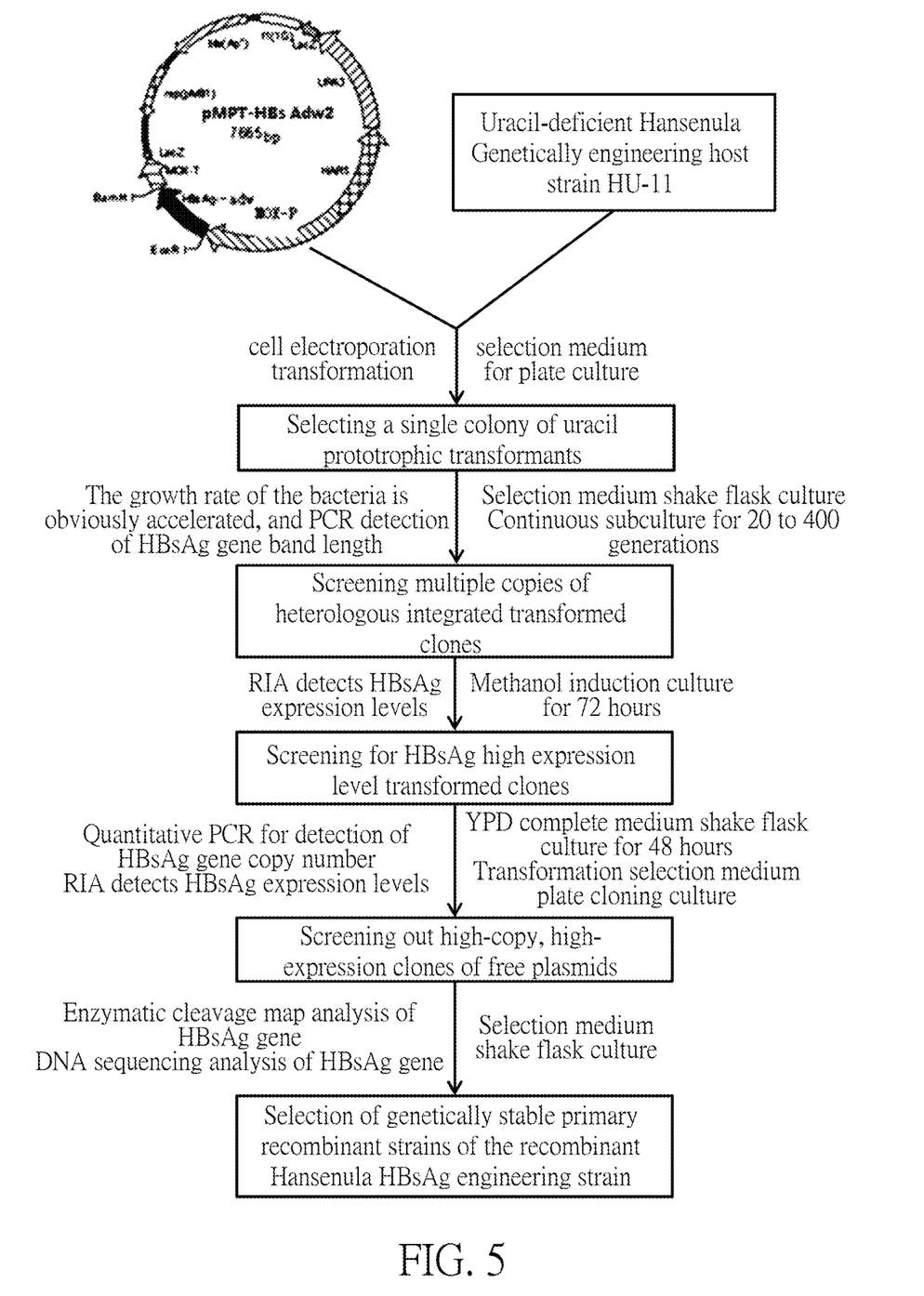
FIG. 5 is a flow chart showing the steps of transformation and screening of recombinant *Hansenula polymorpha* in Example 2.

The transformation and screening process of recombinant Hansenula polymorpha hepatitis B vaccine was shown in FIG. 5:

1) The pMPT-HBsAg plasmid was transformed into the URA3-auxotrophic Hansenula polymorpha cell strain HU-11 (CGMCC No. 1218) of the host cell by cell electroporation. The culture medium was selected using a selection medium (MD liquid medium). The single colony transformants were picked up on the MD selection culture plate and transferred to the MD liquid medium for continuous subculture. The adw2 subtype HBsAg gene and the corresponding regulatory components were multi-copy and heterologously integrated into the host Hansenula polymorpha cell chromosome.

2) Strain screening included the following steps:

(1) Selecting a single colony of uracil prototrophic transformants

Colonies with rapid growth rate of bacteria were selected. PCR was used to detect the brightness of HBsAg gene bands. Colonies with a large number of copies were selected, and single colonies were shake-cultured in a selective medium, and successively subcultured for 20 to 400 generations;

(2) Screening multiple copies of heterologous integrated transformed clones

After subculture in step (1), after 72 hours of methanol-induced culture, the expression level of HBsAg released by the disruption of transformant cells was determined by radio immunoassay or radioimmunoassay (RIA);

(3) Screening out high-copy, high-expression clones of free plasmids

The clones screened by step (2) were cultured in YPD complete medium for 48 hours, and then transferred into a selection medium plate for cloning culture, and the HBsAg gene copy number was detected by quantitative PCR, and the expression level of HBsAg was detected by RIA.

(4) Based on the detection result of the step (3), the primary strain of the genetically stabilized recombinant *Hansenula polymorpha* HBsAg engineering strain was selected.

Third Embodiment

The main process of 30 liters of pilot fermentation:
1) Strain stored in liquid nitrogen was thawed by 200 ml seed medium, inoculated into the medium, divided into two 0.5 L shake flasks, and cultured at 31° C. for 22 hours as a first-class seed;
2) The primary seed was transferred into the secondary seed culture medium with 1600 ml seed medium, divided into six 1 L shake flasks, and incubate at 31° C. for 20 hours as a secondary seed;
3) 12 L fermentation medium was adjusted to pH 5.5 and transferred into a 30 L fermenter, and then the secondary seed was inoculated under growing at 30-31° C. through two sources of glycerol and methanol; growth, de-repression and induction for the three phases, and co-culture 85 to 96 hours, the cells were harvested after 2-3 hours stopped induction. The frozen cells are homogenized.

Operation Points:
(1) The feeding operation of the growth phase was going when the dissolved oxygen was consumed and the basal medium was consumed; the flow acceleration was gradually increased as the consumption of the basic medium increases, and the flow was added before 2-3 hours the dissolved oxygen was recovered.
(2) In the later stage of the growth phase, pay attention to the dissolved oxygen recovery, record the lowest value of dissolved oxygen, and start to flow when the dissolved oxygen rises to 70-80%, and enter the de-repression phase.
(3) After the later stage of the de-repression phase, the dissolved oxygen began to rise after the end of the flow. When the dissolved oxygen was raised to 70-80% c/o, the methanol induction solution was added, and the methanol concentration is controlled at 3-5; the flow acceleration was controlled by the methanol detection flow controller.
(4) Stopping methanol addition before 2-3 hours the end of fermentation to reduce methanol residue during cell harvest.

Medium

1. Preparation of calcium chloride solution
11.33 g $CaCl_2$ was accurately weighed and put it into a cleaned triangular flask, deionized water was appropriately added to dissolve and dilute to 200 ml.

2. Preparation of Micro Element Solution
Accurately weighting the following reagents:

| | |
|---|---|
| $(NH_4)_2Fe(SO_4)_2 \cdot e(_2O$ | 1000 mg |
| $CuSO_4 \cdot _2O$ | 80 mg |
| $ZnSO_4 \cdot _2O$ | 300 mg |
| $MnSO_4 \cdot _2O$ | 400 mg |
| EDTA | 1000 mg |

The weighed reagent was placed in a cleaned triangular flask, dissolved in deionized water and dissolved to 200 ml.

3. Preparation of Vitamin Solution
Accurately weighting the following reagents:

| | |
|---|---|
| d-Biotin | 6 mg |
| Thiamin HCl | 2000 mg |

Biotin was first dissolved in 10 ml of 50% isopropanol, and then dissolved in Thiamin HCl, and then dissolved in an appropriate amount of deionized water to a volume of 100 ml.

4. Preparation of Trace Element Solution
Accurately weighting the following reagents:

| | |
|---|---|
| $NiSO_4 \cdot _2O$ | 10 mg |
| $CoCl_2 \cdot _2O$ | 10 mg |
| $H_3BO_3$ | 10 mg |
| $Na_2MoO_4 \cdot oO_2O$ | 10 mg |
| KI | 10 mg |

The weighed reagent was placed in a cleaned triangular flask, and an appropriate amount of deionized solution was added to a volume of 50 ml.

The above four solutions were separately sterilized and filtered for use.

5. Preparation of Seed Salt Solution
Accurately weighting the following reagents:

| | |
|---|---|
| $NH_4H_2PO_4$ | 80 g |
| $MgSO_4 \cdot gS_2O$ | 18 g |
| KCl | 20 g |
| NaCl | 2 g |

The weighed reagent was placed in a cleaned triangular flask, dissolved in deionized water and dissolved to a volume of 1600 ml.

6. 27 g of glycerin was weighted in a 2000 ml flask, mixed with a salt solution of 360 mL, and made up to 1800 ml with deionized water. The same amount was dispensed into two 2000 ml flasks, and autoclaved at 110° C. for 30 minutes.

Two empty 500 ml triangle bottles, six 1000 ml triangle bottles, a 100 ml graduated cylinder and a 500 ml graduated cylinder all were sterilized under 110° C., 30 minutes high pressure steam.

7. Primary Seed Medium
In the clean bench, 100 ml of each sterilized glycerin solution was taken aseptically, and added separately into two 500 ml sterilized flasks, and respectively added the following:

| | |
|---|---|
| Calcium chloride solution | 1 ml |
| Micro element solution | 1 ml |
| Vitamin solution | 0.5 ml |
| Trace element solution | 0.25 ml |
| Shaking the above solution. | |

8. Secondary Seed Medium
1600 ml of sterilized glycerin solution was placed in a clean bench with sterile operation technique and placed in a 2000 ml sterilized triangle, and separately added:

| | |
|---|---|
| Calcium chloride solution | 16 ml |
| Micro element solution | 16 ml |
| Vitamin solution | 8 ml |
| Trace element solution | 4 ml |

9. Fermentation Medium
The following reagents were accurately weighted and dissolved in 2000 ml of deionized water.

| | |
|---|---|
| $NH_4H_2PO_4$ | 175 g |
| $MgSO_4 \cdot gS_2O$ | 40 g |
| KCl | 44 g |
| NaCl | 4.4 g |

520 g glycerin was weighted and added into a small 500 ml beaker. 10 ml defoamer was added into the beaker to sterilize, and then added:

| | |
|---|---|
| Calcium chloride solution | 175 ml |
| Micro element solution | 175 ml |
| Vitamin solution | 88 ml |
| Trace element solution | 44 ml |

10. Feed Medium 87 g $NH_4H_2PO_4$, 260 g glycerin and 500 ml deionized water were added into 1000 ml flask, and then wrapped feed line and sterilized at 110° C. for 30 minutes.

11. De-Repression Solution 1800 g glycerin and 660 ml deionized water were added into a 5000 ml flask, and then wrapped feed line and sterilized at 110° C. for 30 minutes. 540 ml filter-sterilized salt solution was added after cooling.

12. Induction Solution 400 ml glycerin was added into a 1000 ml flask, and then wrapped feed line and sterilized at 110° C. for 30 minutes. 1600 ml methanol was added aseptically after cooling.

Fourth Embodiment

Purification

The fermentation broth obtained from the third embodiment was harvested and the cells were washed. The detailed steps of purification can be found in References: Li Jin, Kong Yan. Recombinant Hepatitis B Vaccine Production Process. See Li Jin, Yu Yu, Dong Dexiang Editor: Biopharmaceutical Equipment And separation and purification techniques. 1st edition. Beijing: Chemical Industry Press, 2003: 348-349. The harvested cells can be crushed by a homogenizer to release HBsAg; the cell debris was removed by filtration with a 0.22 g microporous filter; the small molecular impurities were removed by ultrafiltration with a 300K ultramicrofilter; and the HBsAg was extracted by silica gel adsorption treatment. Finally, it was purified by butyl agarose hydrophobic chromatography.

REFERENCES

1, Qi Xiaoqiu, etc., the national population of hepatitis B virus epidemiology investigation report, the first edition of April 2011, People's Health Publishing House.
2, Zhuang Hui, China's hepatitis B prevention and treatment status and goals, 2008, meeting.
3. Li Jian et al. Low/no response study after neonatal vaccination with recombinant hepatitis B vaccine (yeast) in Shanghai, China Vaccine and Immunity, 2011, Vol. 17 No. 5: 399-403.
4. Liu Jiaye et al. Comparative study on the immune response and its influencing factors of 20 µg recombinant hepatitis B vaccine in adults, Chinese Journal of Vaccines and Immunity, 2013, Vol. 19, No. 2: 142-146.
5. European Consensus Group on Hepatitis B Immunity. Are booster immunisations needed for lifelong hepatitis B immunity? Lancet 2000; 355: 561-565.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A hepatitis B vaccine comprising a recombinant *Hansenula polymorpha*, comprising and expressing hepatitis B surface antigen (HBsAg) of SEQ ID NO: 1, wherein a host *Hansenula polymorpha* cell line of the recombinant *Hansenula polymorpha* is HU-11, and the accession number of the host *Hansenula polymorpha* cell line is CGMCC No.1218, and a disrupted DNA sequence of an orotidine-5-phosphate decarboxylase gene of the host Hansenula polymorpha is SEQ ID NO: 3, wherein the dose of the HBsAg in the hepatitis B vaccine is 40 pg/dose for adults and 20 pg/dose for children, and wherein the pure stock solution yield of the hepatitis B vaccine is 300 mg/L fermentation liquid to 400 mg/L fermentation liquid.

2. The hepatitis B vaccine comprising a recombinant *Hansenula polymorpha* according to claim 1, wherein the amino acid sequence of the HBsAg expressed by the recombinant *Hansenula polymorpha* is shown in SEQ ID NO: 2.

3. The hepatitis B vaccine comprising a recombinant *Hansenula polymorpha* according to claim 1, wherein the HBsAg expressed by the recombinant *Hansenula polymorpha* is a virus-like particle structure, which is formed by inserting HBsAgs into *Hansenula polymorpha* lipid, and wherein 9 to 12 among the 14 cysteic acids of the HBsAg form disulfide bonds.

4. The hepatitis B vaccine comprising a recombinant *Hansenula polymorpha* according to claim 1, wherein the hepatitis B vaccine further comprises an adjuvant; the adjuvant is aluminum adjuvant prepared by in-situ coprecipitation or the direct adsorption; the aluminum adjuvant is preferably prepared by in-situ coprecipitation.

5. The hepatitis B vaccine comprising a recombinant *Hansenula polymorpha* according to claim 1, wherein the immunization procedure of the high dosage of hepatitis B vaccine is one injection respectively in 0, 1, 2 to 12 months for three needles; the preferably immunization procedure is one injection respectively in 0, 1, and 6 months for three needles.

6. The hepatitis B vaccine comprising a recombinant *Hansenula polymorpha* according to claim 1, wherein the dosage form of the hepatitis B vaccine is selected form prefilled injection solution, injection solution or lyophilized powder injection; the dosage form is preferably the prefilled injection solution.

7. The hepatitis B vaccine comprising a recombinant *Hansenula polymorpha* according to claim 1, wherein the hepatitis B surface antigen is adw subtype.

8. A recombinant *Hansenula polymorpha*, wherein the recombinant *Hansenula polymorpha* comprises the nucleotide sequence of SEQ ID NO: 1, and the nucleotide sequence of SEQ ID NO: 1 is integrated into the genome of the recombinant *Hansenula polymorpha*, wherein a host *Hansenula polymorpha* cell line of the recombinant *Hansenula polymorpha* is HU-11, and the accession number of the host *Hansenula polymorpha* cell line is CGMCC No.1218, and a disrupted DNA sequence of an orotidine-5-phosphate decarboxylase gene of the host *Hansenula polymorpha* is SEQ ID NO: 3.

9. The hepatitis B vaccine comprising a recombinant *Hansenula polymorpha* according to claim 3, wherein the HBsAg expressed by the recombinant *Hansenula polymorpha* is a virus-like particle structure, which is formed by inserting HBsAgs into *Hansenula polymorpha* lipid, and wherein 9 to 12 among the 14 cysteic acids of the HBsAg form disulfide bonds.

10. The hepatitis B vaccine comprising a recombinant *Hansenula polymorpha* according to claim 3, wherein the hepatitis B vaccine further comprises an adjuvant; the adjuvant is aluminum adjuvant prepared by in-situ coprecipitation or the direct adsorption; the aluminum adjuvant is preferably prepared by in-situ coprecipitation.

11. The hepatitis B vaccine comprising a recombinant *Hansenula polymorpha* according to claim 4, wherein the hepatitis B vaccine further comprises an adjuvant; the adjuvant is aluminum adjuvant prepared by in-situ coprecipitation or the direct adsorption; the aluminum adjuvant is preferably prepared by in-situ coprecipitation.

* * * * *

SEQUENCE LISTING

```
<160> NUMBER OF SEQ ID NOS: 3

<210> SEQ ID NO 1
<211> LENGTH: 681
<212> TYPE: DNA
<213> ORGANISM: Artificial sequence
<220> FEATURE:
<223> OTHER INFORMATION: the sequence is synthesized

<400> SEQUENCE: 1
atggagaaca tcacttcagg gtttctagga cctctcctgg tgttgcaggc gggcttcttc    60
ctgttgaccc gaatcctcac cataccgcag agtctggata gctggtggac gtctctcaac   120
tttctcggcg gctccctgt ctgtctcggc cagaactcgc aatccctac ctctaaccac      180 tcgccaacct cttgtcctcc aatttgtcca ggttaccgct ggatgtgtct gaggcggttt   240 atcattttc tcttcatctt gctcctgtgc cttatcttct tgttggtgct gcttgactat    300
cagggcatgt tgccagtctg ccctctgatc cctggatcta ctacgaccag cactggtcca   360
tgcaagacgt gcactacccc cgcccaagga aactccatgt tcccctcctg ctgttgcacg   420
aagcctaccg acggcaattg cacctgcatc ccgatccat cgtcgtgggc attcgctaag    480
tatctgtggg agtgggccag cgtcagattc tcttggctct cccttctagt gccattcgtc    540
```
caatggttcg taggccttc cccgactgtt tggctttccg ccatttggat gatgtggtat    600
tggggtccat cgctctacag cattgttagt cccttatcc cactgctgcc cattttcttt    660
tgcctttggg tttacatcta a    681

<210> SEQ ID NO 2
<211> LENGTH: 226
<212> TYPE: PRT
<213> ORGANISM: Artificial sequence
<220> FEATURE:
<223> OTHER INFORMATION: the sequence is synthesized

<400> SEQUENCE: 2

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ser Pro Val Cys
        35                  40                  45

Leu Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Thr Thr Thr Ser Thr Gly Pro Cys Lys Thr Cys Thr Thr Pro Ala
        115                 120                 125

Gln Gly Asn Ser Met Phe Pro Ser Cys Cys Cys Thr Lys Pro Thr Asp
    130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Ala Ile Trp Met Met Trp Tyr Trp Gly Pro Ser Leu Tyr Ser Ile
        195                 200                 205

Val Ser Pro Phe Ile Pro Leu Leu Pro Ile Phe Phe Cys Leu Trp Val
    210                 215                 220

Tyr Ile
225

<210> SEQ ID NO 3
<211> LENGTH: 797
<212> TYPE: DNA
<213> ORGANISM: Artificial sequence
<220> FEATURE:
<223> OTHER INFORMATION: the sequence is synthesized

<400> SEQUENCE: 3
atgtataaat cttatggaga aagggcgaag tgaagtctca cccatctaag gtcgccagca    60
gactacttaa tttgatggaa tccaagcaaa caaacctctg cgcttctgtg gatgtgacta   120
aaactcagga attattggag cttcttgata aactgggccc ttacatctgc cttgtcaaaa   180
ctcatattga catagtagag gacttctctt atgaacacac catttttacca ttacaggact   240

```
tgcaaagaaa cacaacttca tgatttttga agacagaaag tttgctgata ttaggaaaca    300
cagtcaaact acagtataag ggaggaattt atcgaacatc caagtgggcc gatatcacga    360
atgcacacgg agtgactggc gcaggaattg ttgaaggtct taaacaggcc gcagaagaaa    420
gtacagatga gccacgtggg cttttgatgc ttgctgagct ctcttcaaag ggatcattag    480
ctaccggtga gtatactcaa aaaactgtgg aaatagcgaa aagcgataaa gaatttgtca    540
ttggatttat tgcacagaga gacatgggag gtcgtgagga aggctttgac tggctgatca    600
tgactccagg agttggttta gatgataaag gtgattctct gggccaacag tacagaactg    660
ttgatgaagt gatgcaaaca ggaaccgatg tcattatcgt tggaagaggt ttattcggaa    720
aaggaagaga tcctgaagtg gaagggaaga gatacagaaa tgctgggtgg gaagcttaca    780
agcggcgcat tgcttaa                                                  797
```